(12) United States Patent
Shigemori et al.

(10) Patent No.: US 8,002,693 B2
(45) Date of Patent: Aug. 23, 2011

(54) RECEIVING APPARATUS

(75) Inventors: Toshiaki Shigemori, Hachioji (JP);
Manabu Fujita, Hino (JP); Ayako Nagase, Hachioji (JP); Akira Matsui, Hino (JP); Kazutaka Nakatsuchi, Hino (JP)

(73) Assignees: Olympus Medical Systems Corporation (JP); Olympus Corporation (JP)

(*) Notice: Subject to any disclaimer, the term of this patent is extended or adjusted under 35 U.S.C. 154(b) by 1211 days.

(21) Appl. No.: 11/571,421

(22) PCT Filed: Sep. 1, 2006

(86) PCT No.: PCT/JP2006/317375
§ 371 (c)(1),
(2), (4) Date: Dec. 28, 2006

(87) PCT Pub. No.: WO2007/026891
PCT Pub. Date: Mar. 8, 2007

(65) Prior Publication Data
US 2009/0005642 A1 Jan. 1, 2009

(51) Int. Cl.
*A61B 1/00* (2006.01)
(52) U.S. Cl. .......... 600/101; 600/118
(58) Field of Classification Search .......... 600/118, 600/117, 160, 302, 101; 455/130; 375/316
See application file for complete search history.

(56) References Cited

U.S. PATENT DOCUMENTS

| | | | | |
|---|---|---|---|---|
| 4,963,960 A | * | 10/1990 | Takami | 348/69 |
| 5,493,498 A | * | 2/1996 | Miyoshi | 701/208 |
| 5,923,919 A | * | 7/1999 | Nimura et al. | 399/37 |
| 6,397,086 B1 | * | 5/2002 | Chen | 455/569.2 |
| 6,924,607 B2 | * | 8/2005 | Cash et al. | 315/307 |
| 2002/0032366 A1 | | 3/2002 | Iddan et al. | |
| 2003/0088160 A1 | * | 5/2003 | Halleck et al. | 600/300 |
| 2003/0093503 A1 | * | 5/2003 | Yamaki et al. | 709/220 |
| 2004/0087832 A1 | * | 5/2004 | Glukhovsky et al. | 600/118 |
| 2004/0170398 A1 | * | 9/2004 | Nishigaki | 386/125 |
| 2004/0175289 A1 | | 9/2004 | Takizawa | |
| 2005/0004473 A1 | * | 1/2005 | Fujita et al. | 600/476 |
| 2005/0049488 A1 | * | 3/2005 | Homan | 600/431 |

(Continued)

FOREIGN PATENT DOCUMENTS

EP 1 422 677 5/2004

(Continued)

OTHER PUBLICATIONS

European Search Report dated Apr. 28, 2010.

(Continued)

*Primary Examiner* — John P Leubecker
(74) *Attorney, Agent, or Firm* — Ostrolenk Faber LLP (57) ABSTRACT

A condition for determining that an examination by a capsule endoscope 3 (body insertable device) completes is set in advance. When a predetermined time period has passed since the examination starts, and when received electric-field strength of receiving antennas A1 to An detected during a predetermined time period is not higher than a predetermined value, the examination is determined to have been completed. An examination completion determining unit C1 determines whether the condition is satisfied or not. According to the result of determination, a notification controller C2 makes a notifying unit 15 notify that the examination completes, and a power supply controller C3 stop power supply to a radio unit 2a. Thus, unnecessary power consumption is prevented and the completion of the examination by the body insertable device is recognized.

7 Claims, 7 Drawing Sheets

U.S. PATENT DOCUMENTS

2005/0054897 A1* 3/2005 Hashimoto et al. ............ 600/118
2007/0073106 A1* 3/2007 Uchiyama ..................... 600/118

FOREIGN PATENT DOCUMENTS

| | | |
|---|---|---|
| EP | 1600099 | 11/2005 |
| JP | 2003-19111 | 1/2003 |
| JP | 2003-325440 | 11/2003 |
| JP | 2003-325440 A | 11/2003 |
| JP | 2004-167163 | 6/2004 |
| JP | 2004-167163 A | 6/2004 |
| JP | 2004-267350 | 9/2004 |
| JP | 2004-267350 A | 9/2004 |
| JP | 2005-218502 | 8/2005 |
| JP | 2005-218502 A | 8/2005 |
| WO | 96/25877 | 8/1996 |
| WO | WO 2004/078036 | 9/2004 |

OTHER PUBLICATIONS

Australian Office Action dated Jan. 25, 2010 in corresponding Australian Patent Application No. 2006285700 (1 page).
Notification Concerning Availability of Publication issued in connection with corresponding PCT Appln. No. PCT/JP2006/317375 dated Mar. 8, 2007.
International Search Report issued in connection with corresponding PCT Appln. No. PCT/JP2006/317375 dated Nov. 21, 2006.
International Search Report for International Application No. PCT/JP2006/317375 dated Nov. 21, 2006.
Australian Office Action dated Apr. 1, 2009 in connection with corresponding Australian Patent Application No. 2006285700.
International Search Report PCT/JP2006/317375 dated Nov. 7, 2006 (Japanese Patent Office).

* cited by examiner

RECEIVING APPARATUS

CROSS REFERENCE TO RELATED APPLICATION

The present application is a 35 U.S.C. §§371 national phase conversion of PCT/JP2006/317375, filed 1 Sep. 2006, which claims priority of Japanese Patent Application No. 2005-255496 filed 2 Sep. 2005, which is herein incorporated by reference.

TECHNICAL FIELD

The present invention relates to a receiving apparatus which acquires transmission data transmitted from a body insertable device such as a capsule endoscope which is introduced into a subject body and acquires intra-subject information, for example.

BACKGROUND ART

In recent years, a capsule endoscope having an imaging function and a radio communication function appears in a field of endoscope. After being swallowed by a patient, i.e., a subject (human body), from the mouth for an observation (examination), the capsule endoscope travels through inside internal organs (body cavities) such as esophagus, stomach, and small intestine following peristaltic movements and sequentially captures images using the imaging function until naturally discharged from a living body of the patient, in other word, during an observation period.

During the observation period in which the capsule endoscope travels through the internal organs, the capsule endoscope captures images in the body cavities thereby obtaining image data, and sequentially transmits the image data to an outside of the subject body via radio communication, for example, using the radio communication function. The image data received is accumulated in a memory inside an external receiving apparatus. When the patient carries the receiving apparatus equipped with the radio communication function and the memory function, the patient can move freely without inconveniences even after swallowing the capsule endoscope and before discharging the same, i.e., even during the observation period. After the observation finishes, a doctor can display images inside the body cavities on a display unit or the like based on the image data accumulated in the memory of the receiving apparatus, and make diagnosis (see Patent Document 1, for example).

Patent Document 1: Japanese Patent Application Laid-Open No. 2003-19111

DISCLOSURE OF INVENTION

Problem to be Solved by the Invention

However, the receiving apparatus according to Patent Document 1 does not have a notifying unit to notify an end of examination. Therefore, even when the capsule endoscope stops sending electric waves due to battery exhaustion and the examination is terminated halfway, for example, the subject does not notice the end of the examination and keeps on carrying the receiving apparatus, whereby physical burden on the subject may increase. In addition, the power supply to a receiving unit in the receiving apparatus does not stop even after the examination terminates, whereby power is consumed in waste.

In view of the foregoing, an object of the present invention is to provide a receiving apparatus which can prevent unnecessary power consumption. Another object of the present invention is to make it possible to recognize the end of examination by the body insertable device.

Means for Solving Problem

To solve the problems as described above and to achieve an object, according to the present invention, a receiving apparatus includes a receiver which receives transmission data transmitted from a body insertable device; a determiner which determines whether a predetermined condition to determine that an examination completes is satisfied or not; and a power supply controller which controls so that power supply at least to the receiver is cut according to a result of determination by the determiner.

The receiving apparatus may further include a notifier which notifies that the examination completes according to the result of determination by the determiner.

In the receiving apparatus, the receiver may receive the transmission data transmitted from the body insertable device using a receiving antenna, and the receiving apparatus may further include a received electric-field strength detector which detects received electric-field strength of the receiving antenna, and the determiner may determine that the predetermined condition to determine that the examination completes is satisfied, when a predetermined time period has passed since the examination starts, and when the received electric-field strength detected by the received electric-field strength detector during a predetermined time period is not higher than a predetermined value.

In the receiving apparatus, the receiver may receive image data as the transmission data from the body insertable device, and the receiving apparatus may further include an image reception detector which detects that the receiver fails to receive the image data, and the determiner determines that the predetermined condition to determine that the examination completes is satisfied, when the predetermined time period has passed since the examination starts, and when the image reception detector does not detect the reception of the image data for a predetermined time period.

In the receiving apparatus, the receiver may receive image data as the transmission data from the body insertable device, and the receiving apparatus may further include a color distribution detector which detects color distribution of the image data received by the receiver, and the determiner may determine whether the predetermined condition to determine that the examination completes is satisfied or not based on the color distribution detected by the color distribution detector.

In the receiving apparatus, the determiner may regard a start of power supply to the apparatus or a first reception of the transmission data transmitted from the body insertable device by the receiver after the power supply starts, as the start of the examination, and the determiner may regard as that the predetermined time period has passed, when the determiner detects that the predetermined time period has passed after counting of time starts from a start of the examination, or when the determiner detects that a number of transmission data transmitted from the body insertable device at a predetermined transmission rate reaches to a predetermined number.

Effect of the Invention

According to the present invention, the predetermined condition to determine that the examination completes is set in advance, and the determiner determines whether the predetermined condition is satisfied or not, and cuts the power supply to the receiver, which receives the transmission data from the body insertable device, according to the result of determination, whereby an unnecessary power consumption can be prevented.

EXPLANATIONS OF LETTERS OR NUMERALS

1 Subject
2 Receiving apparatus
2a Radio unit
2b Main receiving unit
3 Capsule endoscope
4 Display device
5 Portable recording medium (storage unit)
11 Receiving unit
12 Received electric-field strength detector
13 Image processor
14 Display unit
15 Notifying unit
16 Power supply unit
17 Switching unit
18 Image reception detecting unit
19 Color distribution detecting unit
A1 to An Receiving antenna
C Control unit
C1 Examination completion determining unit
C2 Notification controller
C3 Power supply controller

BEST MODE(S) FOR CARRYING OUT THE INVENTION

Exemplary embodiments of a receiving apparatus according to the present invention will be described in detail below with reference to the drawings of FIGS. 1 to 7. It should be noted that the present invention is not limited to the embodiments and that various modifications can be made without departing from the scope of the present invention.

First Embodiment

Figure 1:
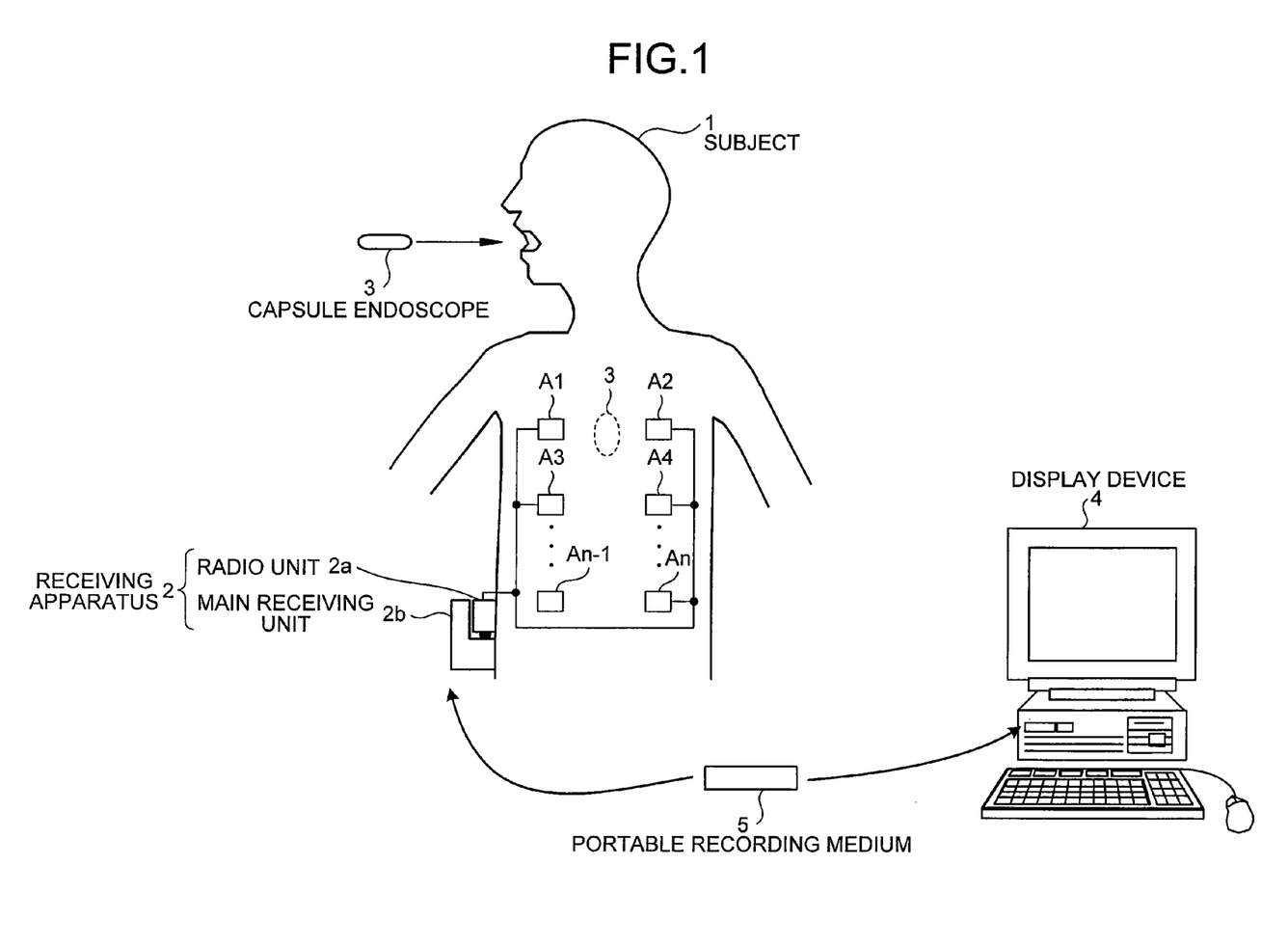
FIG. 1 is a schematic diagram of an overall structure of a wireless in-vivo information acquiring system.

FIG. 1 is a schematic diagram of an overall structure of a wireless in-vivo information acquiring system. The wireless in-vivo information acquiring system includes a capsule endoscope as an example of a body insertable device. As shown in FIG. 1, the wireless in-vivo information acquiring system includes a capsule endoscope 3 which is inserted into a subject 1, captures images inside body cavities, and transmits data such as image signals to a receiving apparatus 2, the receiving apparatus 2 which receives the image data of inside the body cavities when the image data is transmitted from the capsule endoscope 3 by radio, a display device 4 which displays images inside the body cavities based on the image signals received by the receiving apparatus 2, and a portable recording medium 5 which serves for data transfer between the receiving apparatus 2 and the display device 4. The receiving apparatus 2 includes a radio unit 2a which has plural receiving antennas A1 to An attached to an outer surface of the subject body 1, and a main receiving unit 2b which performs, for example, processing of radio signals received by the plural receiving antennas A1 to An. The radio unit 2a and the main receiving unit 2b are detachably connected via a connector or the like. Each of the receiving antennas A1 to An may be provided in a jacket which the subject 1 can wear, for example, and may be indirectly attached to the subject 1 when the subject 1 wears the jacket. Here, the receiving antennas A1 to An may be detachable from the jacket.

The display device 4 serves to display images such as images captured by the capsule endoscope 3 inside the body cavities. The display device 4 has a configuration like a workstation to display images based on the data obtained from the portable recording medium 5. Specifically, the display device 4 may directly display the image on a Cathode Ray Tube (CRT) display, liquid crystal display, or the like. Alternatively, the display device 4 may output the image onto other media as in a printer.

The portable recording medium 5 can be attached to and detached from the main receiving unit 2b and the display device 4, and information can be retrieved from or recorded into the portable recording medium 5 while the portable recording medium 5 is attached to the main receiving unit 2b and the display device 4. In the embodiments, the portable recording medium 5 is attached to the main receiving unit 2b and records data transmitted from the capsule endoscope 3 while the capsule endoscope travels in the body cavities of the subject body 1. After the capsule endoscope 3 is discharged from the subject body 1, in other words, after the imaging inside the subject body 1 is finished, the portable recording medium 5 is removed from the main receiving unit 2b and attached to the display device 4, then the display device 4 reads out the data recorded in the portable recording medium 5. Since the portable recording medium 5 including a Compact Flash (registered trademark) memory or the like transfers data between the main receiving unit 2b and the display device 4, the subject 1 can move more freely during the imaging inside the body cavities, and the time required for data transfer to the display device 4 can be shortened. Here, the portable recording medium 5 is employed for data transfer between the main receiving unit 2b and the display device 4. A manner of data transfer, however, is not limited thereto. For example, the main receiving unit 2b may include other embedded type of recording device, such as a hard disk, and may be connected to the display device 4 by a cable or by radio transmission for data transfer.

Figure 2:
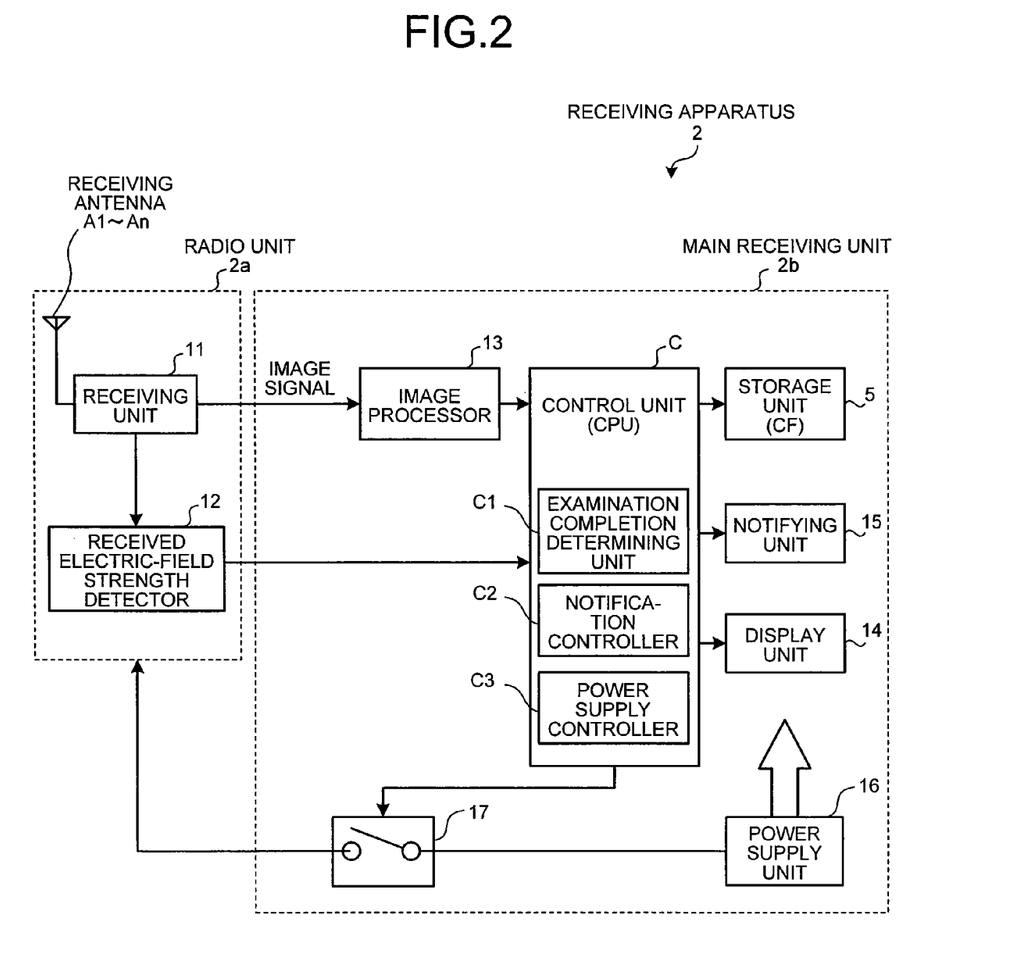
FIG. 2 is a block diagram of a structure of a receiving apparatus according to a first embodiment.

The radio unit 2a and the main receiving unit 2b will be described with reference to FIG. 2. FIG. 2 is a block diagram of a structure of the receiving apparatus 2 according to a first embodiment. The radio unit 2a receives radio signals transmitted from the capsule endoscope 3 and demodulates the received radio signals into base band signals. As shown in FIG. 2, the radio unit 2a includes receiving antennas A1 to An, a receiving unit 11 as a receiver which amplifies and demodulates radio signals received by the receiving antenna, which is selectively connected via switching under the control of a control unit C described later, among the receiving antennas A1 to An, and a received electric-field strength detector 12 which detects received electric-field strength of the receiving antennas A1 to An connected via switching.

The main receiving unit 2b receives and processes the base band signals obtained after the demodulation in the radio unit 2a. As shown in FIG. 2, the main receiving unit 2b includes an image processor 13 connected in a subsequent stage of the receiving unit 11, a display unit 14 which displays image data processed by the image processor 13, the portable recording medium 5, a notifying unit 15 which serves as a notifier that notifies an end of examination, the control unit C which controls each of the above mentioned elements, a power supply unit 16 which includes a battery, for example, that supplies power to the main receiving unit 2b and the radio unit 2a, and a switching unit 17 which connects the radio unit 2a and the power supply unit 16.

The control unit C controls each elements in the receiving apparatus 2, and includes an examination completion determining unit C1 which serves as a determiner that determines that the capsule endoscope 3 swallowed by the subject 1 finishes the examination, a notification controller C2 which controls the operation of the notifying unit 15, and a power supply controller C3 which controls the power supply from the power supply unit 16 to the radio unit 2a.

The receiving unit 11 supplies image signals, which are base band signals obtained through the amplification and demodulation of the radio signals supplied from the receiving antennas, into the image processor 13, and supplies a signal indicating the received electric-field strength of the radio signal received by the receiving antenna to the received electric-field strength detector 12. The received electric-field strength detector 12 detects the received electric-field strength of the receiving antenna based on the above signal and outputs the detected strength to the main receiving unit 2b.

The image data processed by the image processor 13 is stored in the portable recording medium 5 under the control of the control unit C, and displayed on the display unit 14 as necessary. The received electric-field strength signals supplied from the received electric-field strength detector 12 are taken into the control unit C. The examination completion determining unit C1 has an internal timer (not shown) for counting. The examination completion determining unit C1 determines that the examination starts when the power supply to the apparatus starts, for example, and activates the timer to start counting. On detecting that the count reaches a predetermined number indicating a predetermined time period has passed, the examination completion determining unit C1 determines that the predetermined time period has passes.

For example, the examination completion determining unit C1 may determine that the examination starts when the receiving unit 11 receives the transmission data from the capsule endoscope 3 for the first time after the power is on. Further, the examination completion determining unit C1 may determine that the predetermined time period has passed when the examination completion determining unit C1 detects that the number (number of frames) of transmission data (image data) transmitted from the capsule endoscope 3 at a predetermined transmission rate reaches a predetermined number, for example. Since the examination in the body cavities of the subject (human body) 1 with the use of the capsule endoscope 3 usually takes approximately eight hours, the predetermined time period set for the above determination on the completion of the examination may be set to eight hours, for example.

Further, the examination completion determining unit C1 takes in the information on the received electric-field strength as detected by the received electric-field strength detector 12. When the predetermined time period passes after the examination starts, and the received electric-field strength detected by the received electric-field strength detector 12 during a predetermined time period is not higher than a predetermined value, the examination completion determining unit C1 determines that a predetermined condition to determine that the examination completes is satisfied.

The notifying unit 15 includes, for example, an LED, LCD, and speaker, and is controlled by the notification controller C2. The notification controller C2 takes in the result of determination by the examination completion determining unit C1. When the result of determination by the examination completion determining unit C1 satisfies the predetermined condition to determine that the examination completes, the notification controller C2 controls the operation of the notifying unit 15 to make the LED lighten, to make the LCD display a notification, or to make the speaker notify by sound, thereby notifying the user of the completion of the examination. The notifying unit 15 can be replaced with the display unit 14. Then, the notification controller C2 may control the display 14 to present the notification on the screen.

The power supply controller C3 takes in the result of determination by the examination completion determining unit C1. When the result of determination satisfies the predetermined condition to determine that the examination completes, the power supply controller C3 controls the operation of the switching unit 17 and render the switching unit 17 off-state, thereby disconnect the power supply unit 16 from the radio unit 2a. Thus, the power supply controller C3 stops the power supply from the power supply unit 16 to the radio unit 2a.

Figure 3:
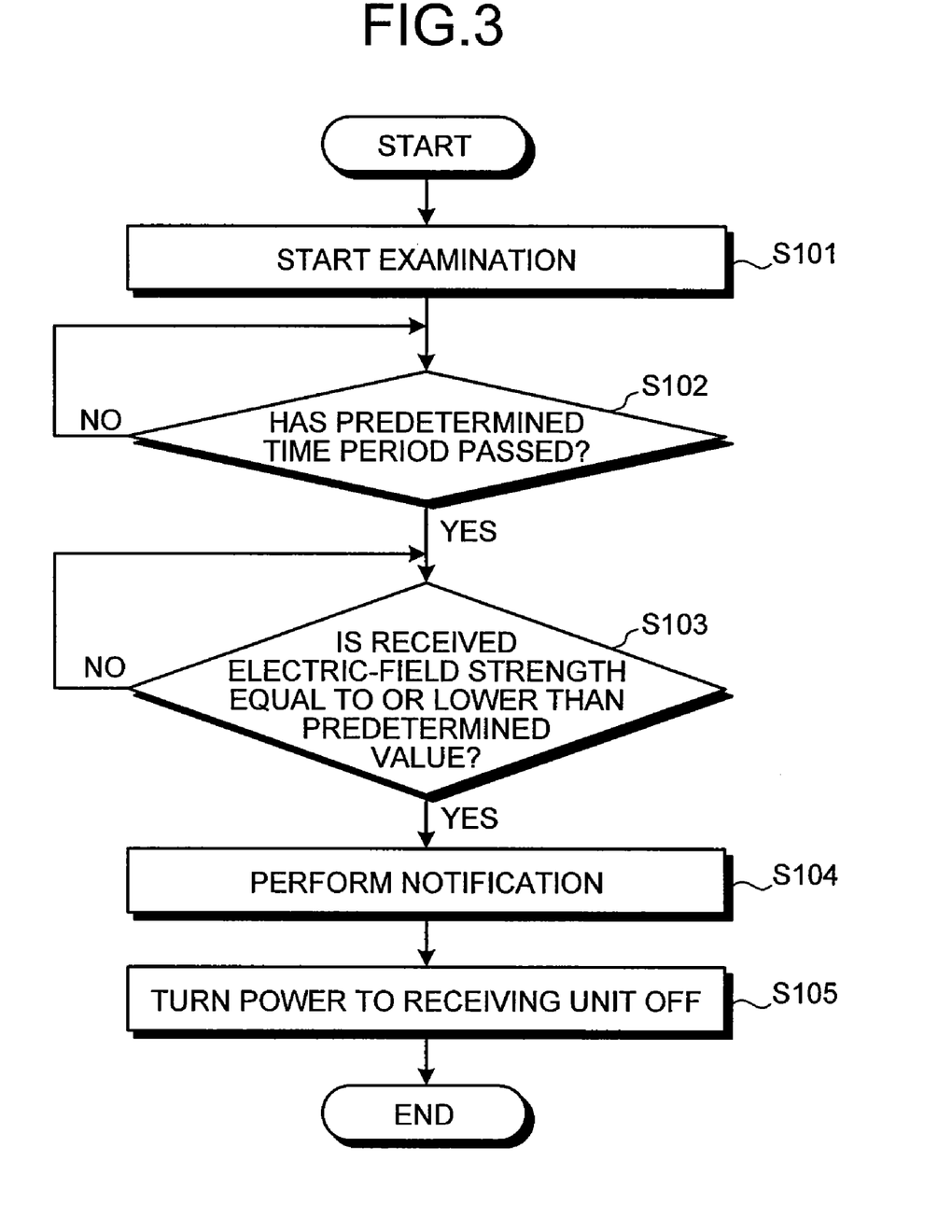
FIG. 3 is a flowchart of an operation of the receiving apparatus shown in FIG. 2.

An operation of the receiving apparatus will be described with reference to the flowchart of FIG. 3. In FIG. 3, the examination completion determining unit C1 determines that the examination has started based on the power supply to the apparatus, for example (step S101), and determines whether the count after the examination start reaches the predetermined time period (step S102). When the examination completion determining unit C1 determines that the predetermined time period has passed since the examination starts in step S102 (Yes in step S102), the examination completion determining unit C1 determines whether the received electric-field strength taken in from the received electric-field strength detector 12 during the predetermined time period is equal to or lower than the predetermined value or not (step S103).

When the examination completion determining unit C1 determines that the received electric-field strength is not higher than the predetermined value in step S103 (Yes in step S103), the examination completion determining unit C1 outputs the result of determination to the notification controller C2 and the power supply controller C3. Then, the notification controller C2 controls the notifying unit 15 and makes the notifying unit 15 performs the notification in the above described manner (step S104). Then, the power supply controller C3 controls the switching unit 17 and turns the same into the off-state, thereby cutting the power supply from the power supply unit 16 to the radio unit 2a, in particular to the receiving unit 11 which consumes large power (step S105).

As can be seen from the foregoing, the receiving apparatus according to the first embodiment determines that the examination completes when the predetermined time period has passed after the examination starts and the received electric-field strength detected during the predetermined time period is not higher than the predetermined value, and notifies the examination completion. Thus, it is possible to recognize that the examination by the capsule endoscope completes. Therefore, the receiving apparatus can be removed from the subject when the examination completes, whereby the physical burden on the subject can be decreased.

In addition, in the first embodiment, on determining that the examination completes, the examination completion determining unit stops the power supply to the radio unit, whereby the radio unit can be prevented from consuming the power (battery) unnecessarily.

Second Embodiment

Figure 4:
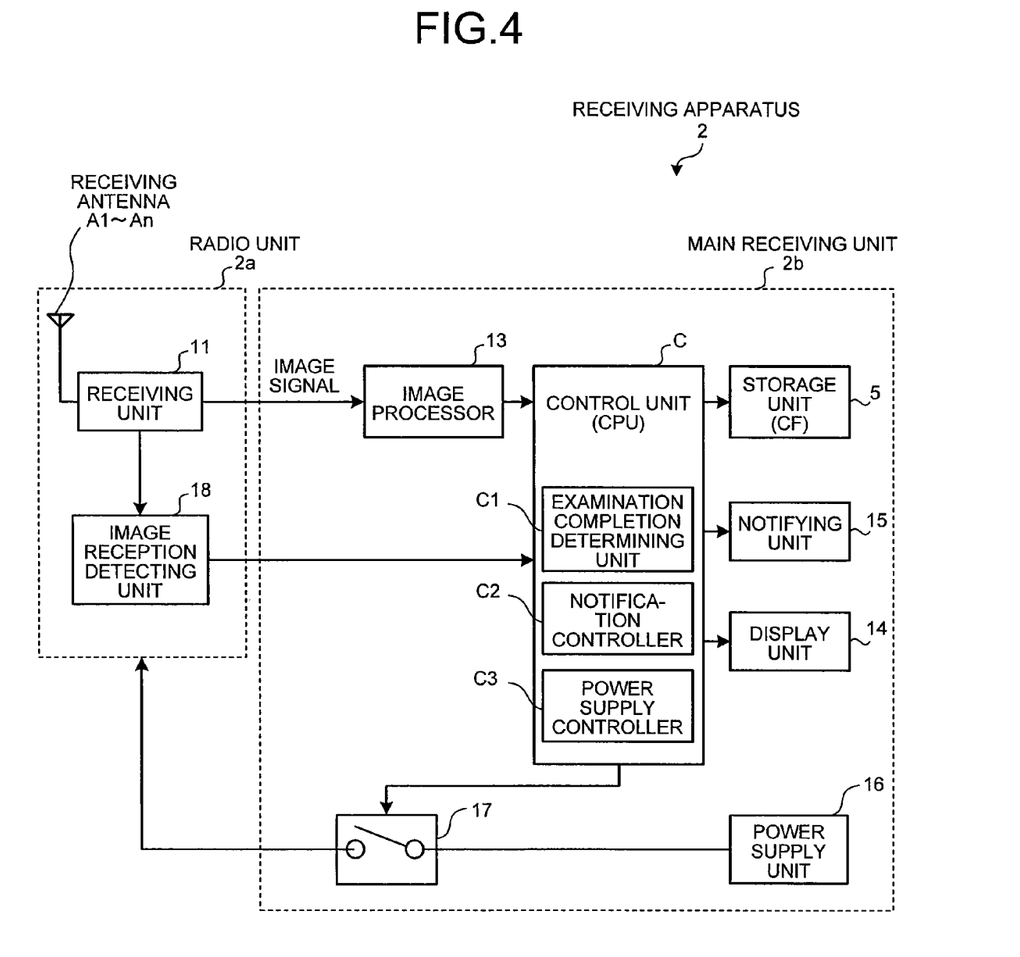
FIG. 4 is a block diagram of a structure of a receiving apparatus according to a second embodiment.

FIG. 4 is a block diagram of a structure of the receiving apparatus 2 according to a second embodiment. The receiving apparatus 2 of the second embodiment is different from the receiving apparatus of the first embodiment in that the receiving apparatus of the second embodiment includes an image reception detecting unit 18 in the radio unit 2a in place of the received electric-field strength detector, and the image reception detecting unit 18 serves as an image reception detector which detects when the receiving unit 11 fails to receive the image data for a predetermined time period. Accordingly, the examination completion determining unit C1 of the second embodiment takes in the result of detection of the image data detected by the image reception detecting unit 18, and determines that a predetermined condition to determine that the examination completes is satisfied when the predetermined time period has passed after the examination starts and there is no image data reception (frame reception) for the predetermined time period.

Figure 5:
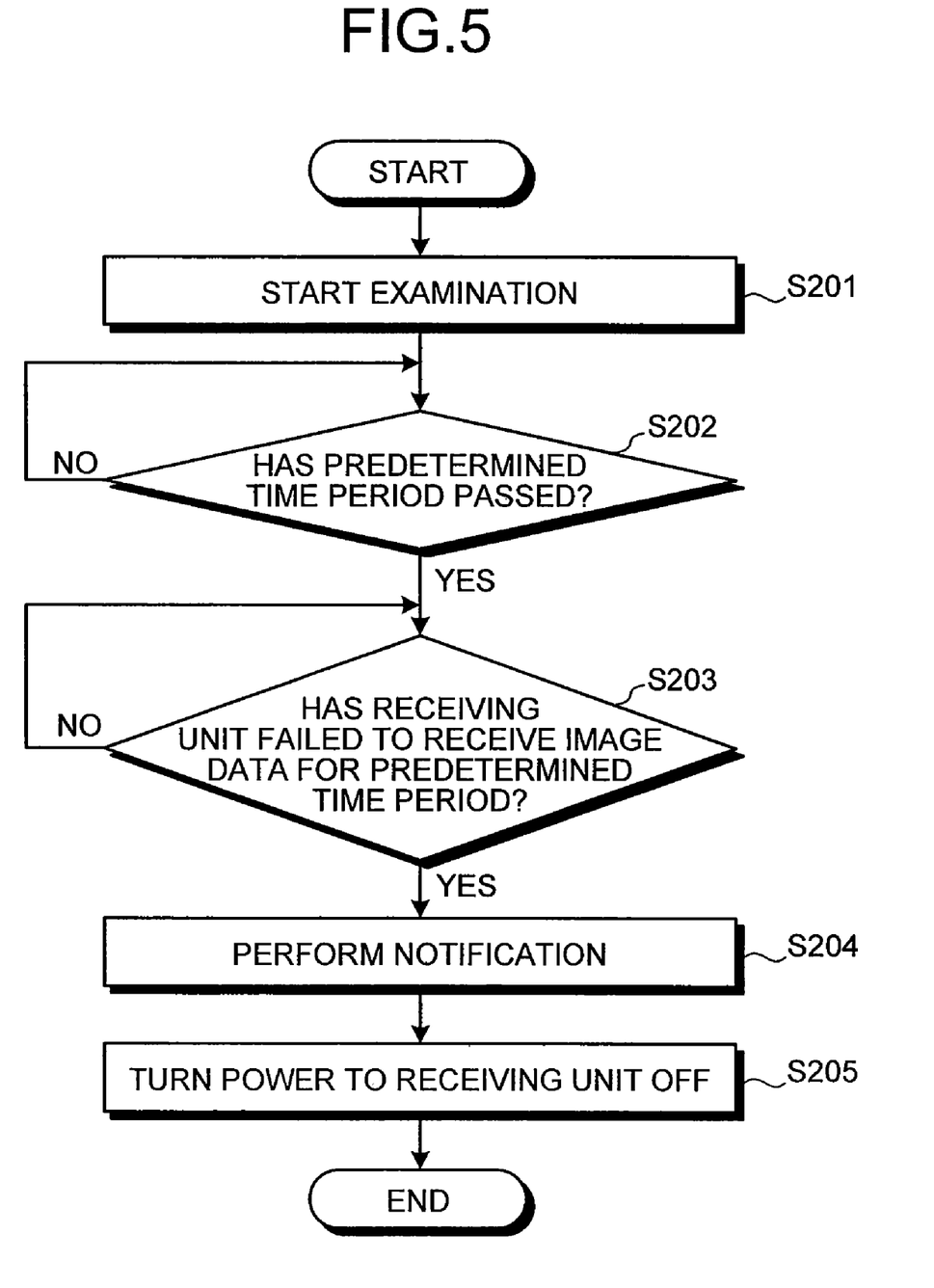
FIG. 5 is a flowchart of an operation of the receiving apparatus shown in FIG. 4.

An operation of the receiving apparatus of the second embodiment will be described with reference to the flowchart of FIG. 5. In FIG. 5, the examination completion determining unit C1 determines whether the examination starts, and then, whether the predetermined time period has passed after the examination starts, similarly to the first embodiment (steps S201, S202). When the examination completion determining unit C1 determines that the predetermined time period has passed after the examination starts in step S202 (Yes in step S202), the examination completion determining unit C1 go on to determine whether the receiving unit 11 fails to receive image data for the predetermined time period or not (step S203).

When the examination completion determining unit C1 determines that the receiving unit 11 fails to receive the image data in step S203 (Yes in step S203), the examination completion determining unit C1 supplies the result of determination to the notification controller C2 and the power supply controller C3. The notification controller C2 controls the notifying unit 15 and makes the notifying unit 15 perform the notification in the above described manner (step S204). The power supply controller C3 controls the switching unit 17 and turns the switching unit 17 into the off-state, thereby cutting the power supply from the power supply unit 16 to the radio unit 2a (step S205).

Thus, in the second embodiment, the receiving apparatus determines that the examination completes when the predetermined time period has passed after the examination starts, and the receiving unit fails to receive the image data for the predetermined time period, and notifies the completion of the examination, whereby it is possible to recognize the completion of the examination by the capsule endoscope. Therefore, the receiving apparatus can be removed from the subject when the examination completes similarly to the first embodiment, and the physical burden on the subject can be reduced.

Further, in the second embodiment, on determining that the examination completes, the examination completion determining unit stops the power supply to the radio unit. Therefore, the radio unit can be prevented from consuming the power (battery) unnecessarily similarly to the first embodiment.

Third Embodiment

Figure 6:
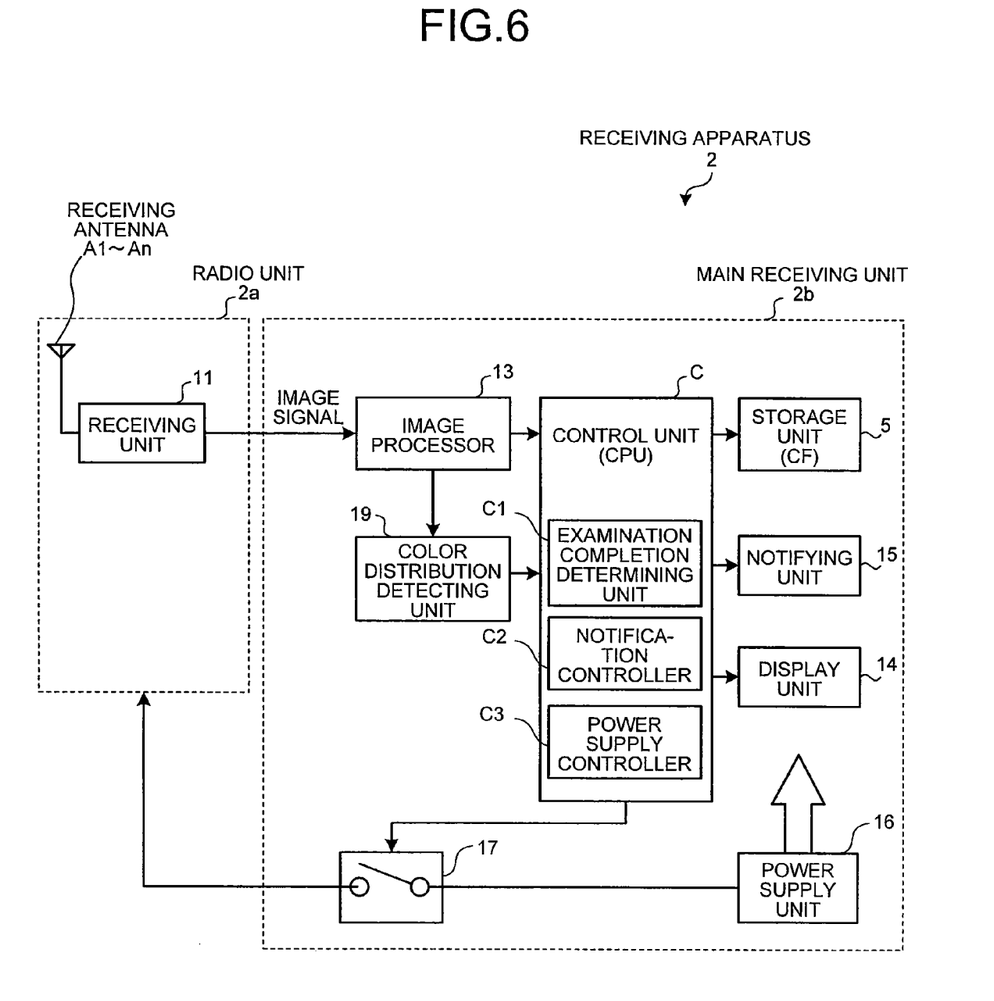
FIG. 6 is a block diagram of a structure of a receiving apparatus according to a third embodiment.

FIG. 6 is a block diagram of a structure of the receiving apparatus 2 according to a third embodiment. The receiving apparatus 2 of the third embodiment is different from the receiving apparatus of the first embodiment in that the receiving apparatus of the third embodiment includes a color distribution detecting unit 19 in the main receiving unit 2b in place of the received electric-field detector, and the color distribution detecting unit 19 serves as a color distribution detector which detects color distribution of the image data processed by the image processor 13. Accordingly, the examination completion determining unit C1 takes in the result of detection of the color distribution of the image data by the color distribution detecting unit 19, and determines that a predetermined condition to determine that the examination completes is satisfied when the detected color distribution does not match with a predetermined color distribution.

The color distribution detecting unit 19 detects color distribution of each image contained in a series of images processed by the image processor 13. For example, the color distribution detecting unit 19 detects an average color. Specifically, the captured image of the organ, in which the examined region resides, shows different color distribution based on the type of the organs. For example, when the average color of the processed image is pale blue, the examined region is esophagus; when the average color of the processed image is red, the examined region is stomach; when the average color of the processed image is yellow, the examined region is small intestine; and when the average color of the processed image is orange, the examined region is large intestine. It is possible to extract substantially uniform color distribution from images of each organ by detecting the average color of each frame, even when the images captured while the capsule endoscope travels through one organ contain noises.

The examination completion determining unit C1 stores a predetermined average color corresponding to each examined region which is an examination target, and compares the average color detected by the color distribution detecting unit 19 with the stored predetermined average color, thereby determining whether the examination completes or not. In comparing the average color, the examination completion determining unit C1 may compare the processed images of the examined region based on color components constituting the average color of the processed image, for example, based on each value of a red color component R, a green color component G, and a blue color component B.

Figure 7:
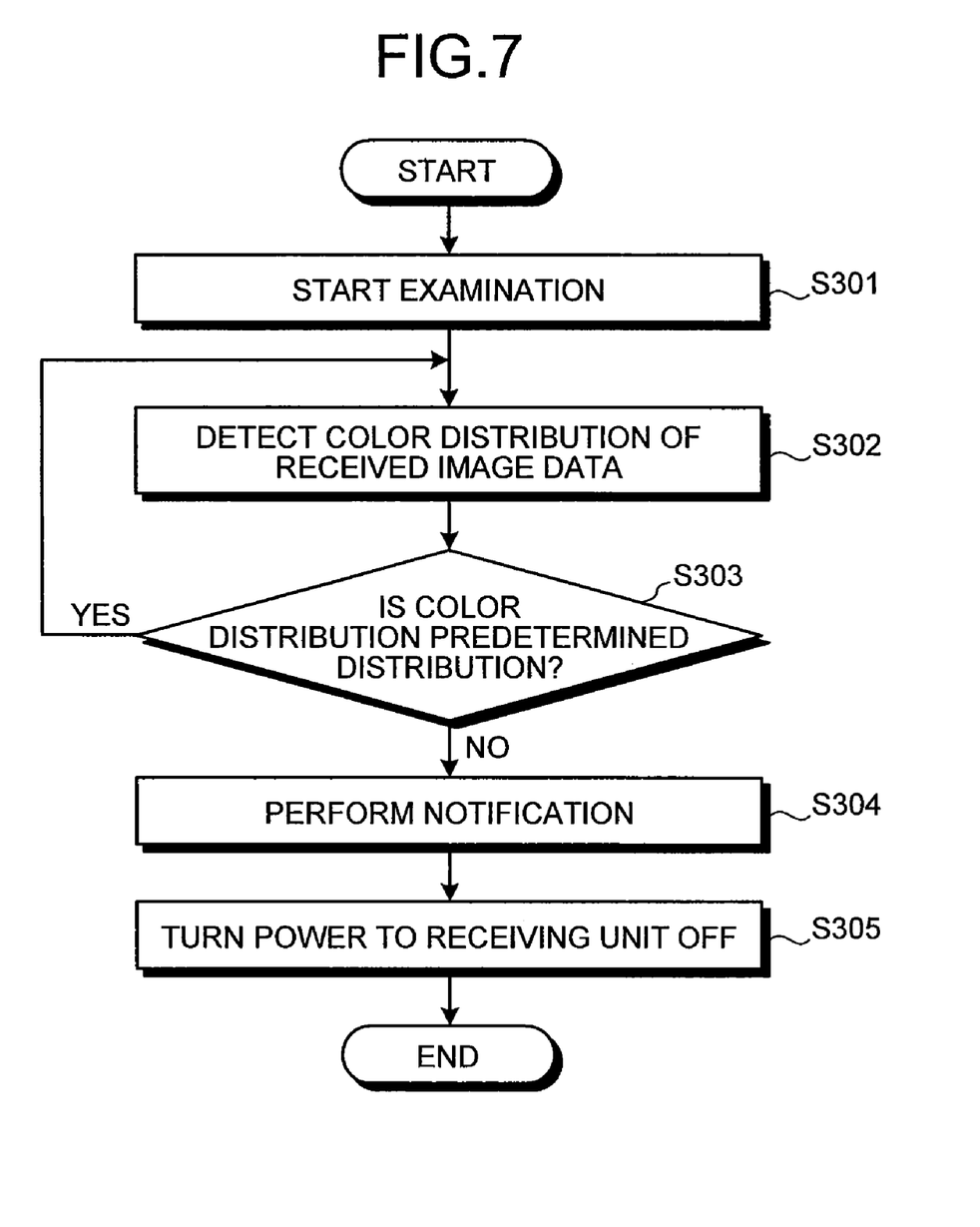
FIG. 7 is a flowchart of an operation of the receiving apparatus shown in FIG. 6.

An operation of the receiving apparatus will be described with reference to the flowchart of FIG. 7. In FIG. 7, the examination completion determining unit C1 determines whether the examination starts, similarly to the first embodiment (step S301). Then, the image processor 13 processes the received image data, and the color distribution detecting unit 19 detects the color distribution (average color) of the processed image (step S302), and further, the examination completion determining unit C1 determines whether the detected average color is identical with the stored predetermined average color or not (step S303).

When the examination completion determining unit C1 determines that the detected average color is different from the predetermined average color of the examined region in step S303 (No in step S303), the examination completion determining unit C1 supplies the result of determination to the notification controller C2 and the power supply controller C3. In response, the notification controller C2 controls the notifying unit 15 and makes the notifying unit 15 perform the notification in the above described manner (step S304). The power supply controller C3 controls the switching unit 17 and turns the switching unit 17 into the off-state, thereby cutting the power supply from the power supply unit 16 to the radio unit 2a (step S305).

As can be seen from the foregoing, in the third embodiment, the receiving apparatus determines that the examination completes when the color distribution of the processed image is different from the predetermined color distribution of the examined region, and notifies the completion of the examination, whereby it is possible to recognize the completion of the examination by the capsule endoscope. Therefore, similarly to the first and the second embodiments, the receiving apparatus can be removed from the subject when the examination completes, and the physical burden on the subject can be reduced.

Similarly to the first and the second embodiments, on determining that the examination completes, the examination completion determining unit of the third embodiment stops the power supply to the radio unit, whereby the radio unit can be prevented from consuming the power (battery) unnecessarily.

In the third embodiment, the predetermined condition for the examination completion determining unit C1 to determine that the examination completes may be, for example, that the predetermined time period has passed since the examination starts, and that the average color detected by the color distribution detecting unit 19 is different from the predetermined average color.

Alternatively, the condition may be that the average color detected by the color distribution detecting unit 19 for a predetermined time period is different from the predetermined average color.

INDUSTRIAL APPLICABILITY

The receiving apparatus according to the present invention is useful for a medical observation apparatus which is introduced into an interior of a human body and employed for an observation of an examined region, and in particular, suitable for preventing unnecessary power consumption.

The invention claimed is:

1. A receiving apparatus comprising:
a receiver which receives transmission data transmitted from a body insertable device;
a determiner which determines whether a predetermined condition to determine that an examination completes is satisfied or not; and
a power supply controller which controls so that power supply at least to the receiver is cut according to a result of determination by the determiner,
wherein
the receiver receives the transmission data transmitted from the body insertable device using a receiving antenna,
the receiving apparatus further comprising:
a received electric-field strength detector which detects received electric-field strength of the receiving antenna, wherein
the determiner determines that the predetermined condition to determine that the examination completes is satisfied, when a predetermined time period has passed since the examination starts, and when the received electric-field strength detected by the received electric-field strength detector during a predetermined time period is not higher than a predetermined value.

2. The receiving apparatus according to claim 1, wherein the determiner regards a start of power supply to the receiving apparatus or a first reception of the transmission data transmitted from the body insertable device by the receiver after the power supply starts, as the start of the examination, and the determiner regards as that the predetermined time period has passed, when the determiner detects that the predetermined time period has passed after counting of time starts from a start of the examination, or when the determiner detects that a number of transmission data transmitted from the body insertable device at a predetermined transmission rate reaches to a predetermined number.

3. A receiving apparatus comprising:
a receiver which receives transmission data transmitted from a body insertable device;
a determiner which determines whether a predetermined condition to determine that an examination completes is satisfied or not; and
a power supply controller which controls so that power supply at least to the receiver is cut according to a result of determination by the determiner, further comprising:
a notifier which notifies that the examination completes according to the result of determination by the determiner, and
wherein
the receiver receives the transmission data transmitted from the body insertable device using a receiving antenna,
the receiving apparatus further comprising:
a received electric-field strength detector which detects received electric-field strength of the receiving antenna, wherein
the determiner determines that the predetermined condition to determine that the examination completes is satisfied, when a predetermined time period has passed since the examination starts, and when the received electric-field strength detected by the received electric-field strength detector during a predetermined time period is not higher than a predetermined value.

4. The receiving apparatus according to claim 3, wherein the determiner regards a start of power supply to the receiving apparatus or a first reception of the transmission data transmitted from the body insertable device by the receiver after the power supply starts, as the start of the examination, and the determiner regards as that the predetermined time period has passed, when the determiner detects that the predetermined time period has passed after counting of time starts from a start of the examination, or when the determiner detects that a number of transmission data transmitted from the body insertable device at a predetermined transmission rate reaches to a predetermined number.

5. A receiving apparatus comprising:
a receiver which receives transmission data transmitted from a body insertable device;
a determiner which determines whether a predetermined condition to determine that an examination completes is satisfied or not; and a power supply controller which controls so that power supply at least to the receiver is cut according to a result of determination by the determiner, wherein the receiver receives image data as the transmission data from the body insertable device, the receiving apparatus further comprising:

an image reception detector which detects that the receiver fails to receive the image data, wherein the determiner determines that the predetermined condition to determine that the examination completes is satisfied, when the predetermined time period has passed since the examination starts, and when the image reception detector does not detect the reception of the image data for a predetermined time period.

6. The receiving apparatus according to claim 5, wherein the determiner regards a start of power supply to the receiving apparatus or a first reception of the transmission data transmitted from the body insertable device by the receiver after the power supply starts, as the start of the examination, and the determiner regards as that the predetermined time period has passed, when the determiner detects that the predetermined time period has passed after counting of time starts from a start of the examination, or when the determiner detects that a number of transmission data transmitted from the body insertable device at a predetermined transmission rate reaches to a predetermined number.

7. A receiving apparatus comprising:

a receiver which receives transmission data transmitted from a body insertable device;

a determiner which determines whether a predetermined condition to determine that an examination completes is satisfied or not; and a power supply controller which controls so that power supply at least to the receiver is cut according to a result of determination by the determiner, wherein the receiver receives image data as the transmission data from the body insertable device, the receiving apparatus further comprising:

a color distribution detector which detects color distribution of the image data received by the receiver, wherein the determiner determines whether the predetermined condition to determine that the examination completes is satisfied or not based on the color distribution detected by the color distribution detector.

* * * * *